United States Patent
Kim

(10) Patent No.: US 6,420,173 B1
(45) Date of Patent: Jul. 16, 2002

(54) **METHOD FOR MASS PRODUCTION AND STORAGE OF SEEDLINGS OF *ELEUTHEROCOCCUS SENTICOSUS* (SIBERIAN GINSENG) THROUGH CELL CULTURING**

(75) Inventor: JaeWhune Kim, Chunjoo-Si (KR)

(73) Assignee: Microplants Co., Ltd., Chonju-Si (KR)

( * ) Notice: Subject to any disclaimer, the term of this patent is extended or adjusted under 35 U.S.C. 154(b) by 0 days.

(21) Appl. No.: 09/578,135

(22) Filed: May 24, 2000

(51) Int. Cl.[7] .................................................. C12N 5/00
(52) U.S. Cl. ........................ 435/410; 435/417; 435/420; 435/430; 435/430.1
(58) Field of Search ................................ 435/410, 417, 435/420, 430, 430.1

(56) References Cited

PUBLICATIONS

Choi, Y.–E. et al., "Structural aspects of somatic embryos derived from cultured zygotic embryos in *Acanthopanax senticosus* L.," *Plant Tissue Culture*, 20:216–226 (1993).

Choi, Y.–E. et al., "Somatic embryogenesis and plant regeneration from suspension cultures of *Acanthopanax koreanum* nakai," *Plant Cell Reports*, 17:84–88 (1997).

Choi, Y.–E. et al., "High frequency of plant production via somatic embryogenesis from callus or cell suspension cultures in *Eleutherococcus senticosus*," *Annals of Botany*, 83:309–314 (1999).

Gui, Y. et al., "Somatic embryogensis and plant regeneration in *Acanthopanax senticosus*," *Plant Cell Reports*, 9:514–516 (1991).

Park, H K, "Germination and growth characteristics of kasiogalpi (*Eleutherococcus senticosus* Max.)," Chonbuk National University, (1997), thesis.

*Primary Examiner*—Leon B. Lankford, Jr.
(74) *Attorney, Agent, or Firm*—Lahive & Cockfield, LLP

(57) ABSTRACT

Disclosed are the mass production of seedlings of *Eleutherococcus senticosus* through cell culturing. *Eleutherococcus senticosus*/embryogenic cells KCTC 0504BP are subcultured to homogeneous sizes of somatic embryos in MS liquid medium.

The somatic embryos are cultured in a bioreactor equipped with an airlift to produce the seedlings or plantlets. The *Eleutherococcus senticosus*/seedlings or plantlets cultured in the bioreactors can be used for extracting components therefrom. The seedlings or plantlets can be eaten and powdered for use in health beverages or tea.

4 Claims, 5 Drawing Sheets

METHOD FOR MASS PRODUCTION AND STORAGE OF SEEDLINGS OF *ELEUTHEROCOCCUS SENTICOSUS* (SIBERIAN GINSENG) THROUGH CELL CULTURING

BACKGROUND OF THE INVENTION

The present invention relates to the production of the seedlings or plantlets of *Eleutherococcus senticosus* (Siberian ginseng). More particularly, the present invention relates to a method for mass producing the seedlings or plantlets of *Eleutherococcus senticosus* through the somatic embryogenesis of *Eleutherococcus senticosus*/embryogenic cells by using bioreactors. In one aspect, the seedlings or plantlets of *Eleutherococcus senticosus* are used as health foods or health aid foods.

*Eleutherococcus senticosus*, which is known as an efficacious medicinal herb all over the world, grows naturally in Korea, China, Japan, and Siberia.

Since the first report of disclosing the value of naturally occurring *Eleutherococcus senticosus* (alias *Acanthopanax senticosus*) as a medicine, researchers in many countries, including Russia, have made efforts to reveal its medicinal components. As a result, acanthoic acid, which is evaluated as being five times more potent in anti-inflammatory activity than is aspirin, β-sitosterol, eleutheroside A-G, and stigmasterol were extracted from *Eleutherococcus senticosus*. By virtue of the cooperation of these medicinal components, *Eleutherococcus senticosus* is now found to effect invigoration, life extension and homeostasis in addition to showing therapeutic activity against hypertension, diabetes, cancer, inflammation, fever and pain, neuralgia, etc, as do Koran ginsengs. Particularly, *Eleutherococcus senticosus* is known to be of sovereign remedy in relieving physical and mental fatigue.

A research report discloses that eleutheroside E, which shows various physiologically active effects, is contained at an amount 1.7~5.5 times greater in the *Eleuthrococcus senticosus* native to Korea than in other native Acanthopanax spp. such as *Acanthopanax chiisanesis, Acanthopanax seoulense, Acanthopanax sieboldianum,* and *Acanthopanax koreanum* (Park, H. K., a thesis for a doctorate, Chonbuk National University, 1997, Korea).

However, *Eleutherococcus senticosus* is difficult for general farm households to seed because of its stringent weather conditions. In addition, the cutting of the plant is not effective for proliferation. Also, because medicinal materials are taken from the velamen and the bark of *Eleutherococcus senticosus*, it takes a long period of time for this shrub to be cultivated to useful extent. What is worse, once the velamen and the bark are taken off, the plant no more maintains its existence. That is, this plant cannot afford reproductive provisions of the medicinal materials, but gives only one chance for getting the medicinal materials.

In the case of ginsengs, success was brought about in mass culturing their cells in culture vessels, enabling the extraction of saponins therefrom (Nitto Denko, Japan). In addition, the cultured bodies are commercially sold as a health food after being dried and powdered in their entirety without processing. As for yew, its cells are cultured to obtain paclitaxel, an anticancer compound.

However, there have been found almost no cases in which the seedlings or plantlets regenerated though cell culturing are mass produced for commercialization as health foods, as in the present invention to be later described in detail.

There are reports regarding the generation of adventitious buds through tissue culture or the regeneration of plants through somatic embryogenesis (Plant Cell Reports 9: 514–516, 1991; Korea J. Plant Tissue Culture 20:216–226, 1993). Achieved only in small scales on agar medium, the techniques disclosed in the reports are different from the present invention in which embryogenic cell strains are established in a broth and used to produce seedlings or plantlets in a large quantity. Until the present invention, there has been reported no research on the system for commercializing *Eleutherococcus senticosus* as health foods or health aid foods by mass producing *Eleutherococcus senticosus* through tissue culture.

SUMMARY OF THE INVENTION

The present invention provides methods that produce seedlings or plantlets of *Eleutherococcus senticosus* in a highly efficient manner. Moreover, the seedlings or plantlets can be used as health foods.

*Eleutherococcus senticosus*/embryogenic cells (Accession number given by the INTERNATIONAL DEPOSITARY AUTHORITY: KCTC 0504BP) are suspension-cultured in MS (Murashige and Skoog) liquid medium under a dark condition to allow the mass proliferation of the embryogenic cells. The invention provides a method for culturing *Eleutherococcus senticosus* seedlings or plantlets, in which embryogenic cells are subcultured to homogeneous sizes of somatic embryos in liquid medium and the somatic embryos in a bioreactor equipped with an airlift are cultured to produce the seedlings or plantlets. The subculturing is carried out repeatedly every 2~3 weeks.

In one embodiment, the proliferated cells are classified according to sizes by filtering them through a network ranging, in pore size, from 150 to 300 µm before the classification. In another embodiment, the embryogenic cells in the filtrate are further suspension-cultured in liquid medium while the embryogenic cell clusters entrapped in the network are subjected to culturing in the bioreactors of liquid medium to be regenerated to the seedlings or plantlets.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

In the present invention, embryogenic cells of *Eleutherococcus senticosus* are suspension-cultured (hereinafter, all suspension cultures are executed at 100 rpm) in an Erlenmeyer flask containing MS medium for 20 days to an extent of tenfold proliferation, after which the cultured cells are allowed to pass through a net with a pore size of 150~300 µm. The passed cells are required to grow further. They are well proliferated in fresh medium. On the other hand, the cell clusters which do not pass through the net are subcultured 4~6 times at intervals of two or three weeks to grow to seedlings or plantlets through somatic embryogenesis in a bioreactor. Then, about 3~4 g of the seedlings or plantlets in wet weight are aseptically transferred to a sterilized petridish containing 1.0% agar medium solidified with deionized water only, and cultured at 25_1° C. for 3~4 days to determine whether they are contaminated or not, after which they, if not contaminated, are packaged into goods which are stored at 8~12° C. in, for example, a refrigerator.

The development from the somatic embryos obtained above to seedlings or plantlets is achievable by use of a bioreactor equipped with an airlift other than by the suspension culture.

Figure 1:
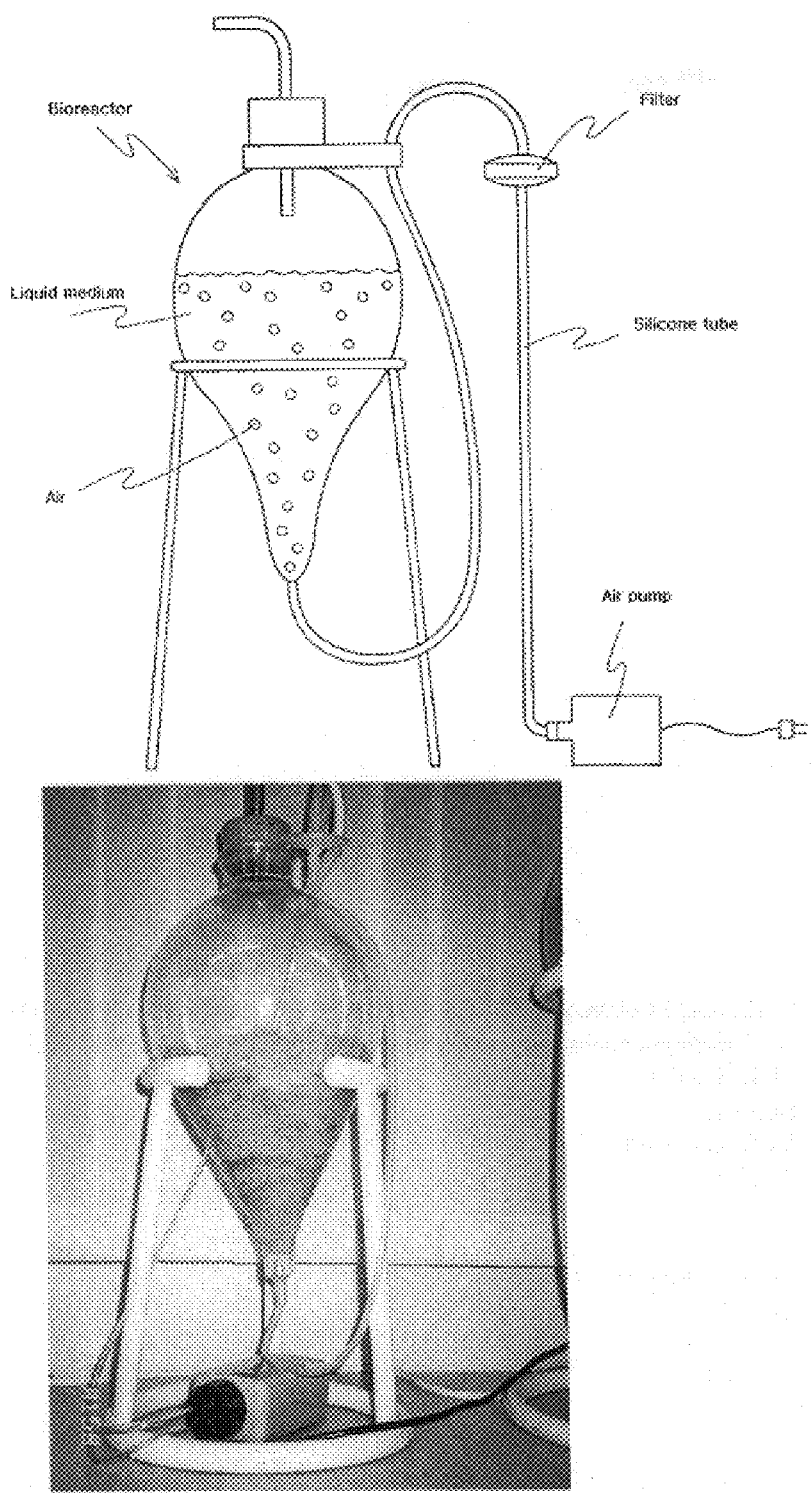
FIG. 1 is photographs showing a bioreactor in which *Eleutherococcus senticosus*/somatic embryos are cultured.

The bioreactor useful in the present invention is equipped with an airlift as shown in FIG. 1. The capacity of the bioreactor is determined depending on the developed state of the somatic embryos: there are no particular limits to the capacity. The introduction of germ-free air into the reactor is accomplished at a lower part of the reactor via airlift externally attached to the reactor. Illustrative, non-limitative examples of the air lift include compressors and air pumps for aquaria. In order to produce germ-free air, the airlift should have a filter with a pore size of not more than 0.2 µm.

A better understanding of the present invention may be obtained in light of the following examples which are set forth to illustrate, but are not to be construed to limit the present invention.

EXAMPLE

Mass Production of Seedlings or Plantlets from
*Eleutherococcus senticosus*/Embryogenic Cells by
Using Bioreactor

Figure 2:
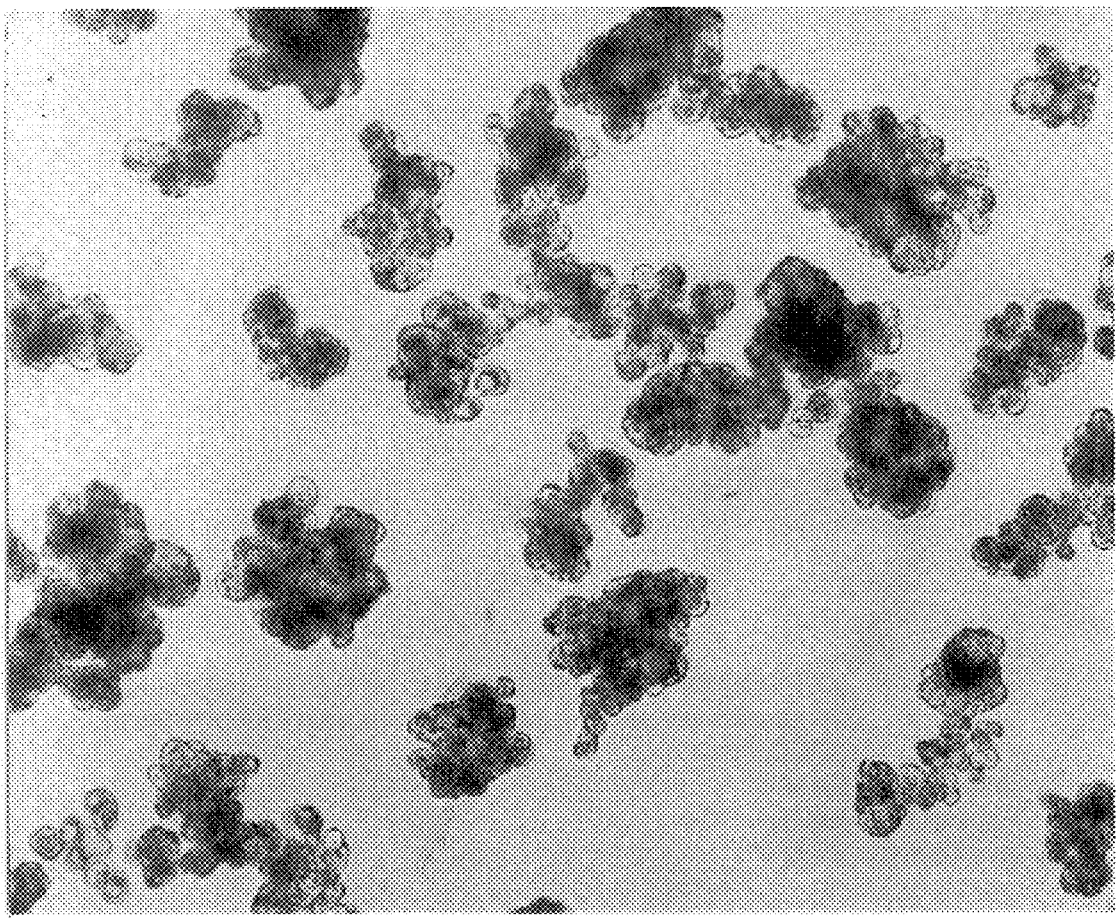
FIG. 2 is a photograph showing *Eleutherococcus senticosus*/embryogenic cells and cell clusters cultured in liquid medium.

*Eleutherococcus senticosus*/embryogenic cells which were deposited in Korean Collection for Type Cultures, Koran Research Institute of Bioscience and Biotechnology on Jul. 14, 1998 at deposition No. KCTC 0504BP, were suspension-cultured at 25_1° C. for 20 days in a 1~2 L Erlenmeyer flask containing 300~800 ml of MS liquid medium (3% sugar, pH 5.8, autoclaved at 121° C. at 1.2 atm) under a dark condition while shaking at 100 rpm. In this culture condition, the embryogenic cells continued to divisionally proliferate to form cell clusters as shown in FIG. 2. At 20 days after culturing, the embryogenic cells gained in wet weight about 10 times greater than before culturing. The cell clusters passed freely through a 150~350 µm network. When cultured in fresh medium in the same manner as previous, these small sized cells could proliferate with maintenance of identical embryogenesis. Therefore, this process makes the *Eleutherococcus senticosus*/embryogenic cells permanently maintained and proliferated.

On the other hand, the embryogenic cell clusters entrapped on the network were transferred to a 3~10 L bioreactor containing MS medium (2.5% sugar) without plant growth regulators and cultured under fluorescent light in the half shade.

Figure 3:
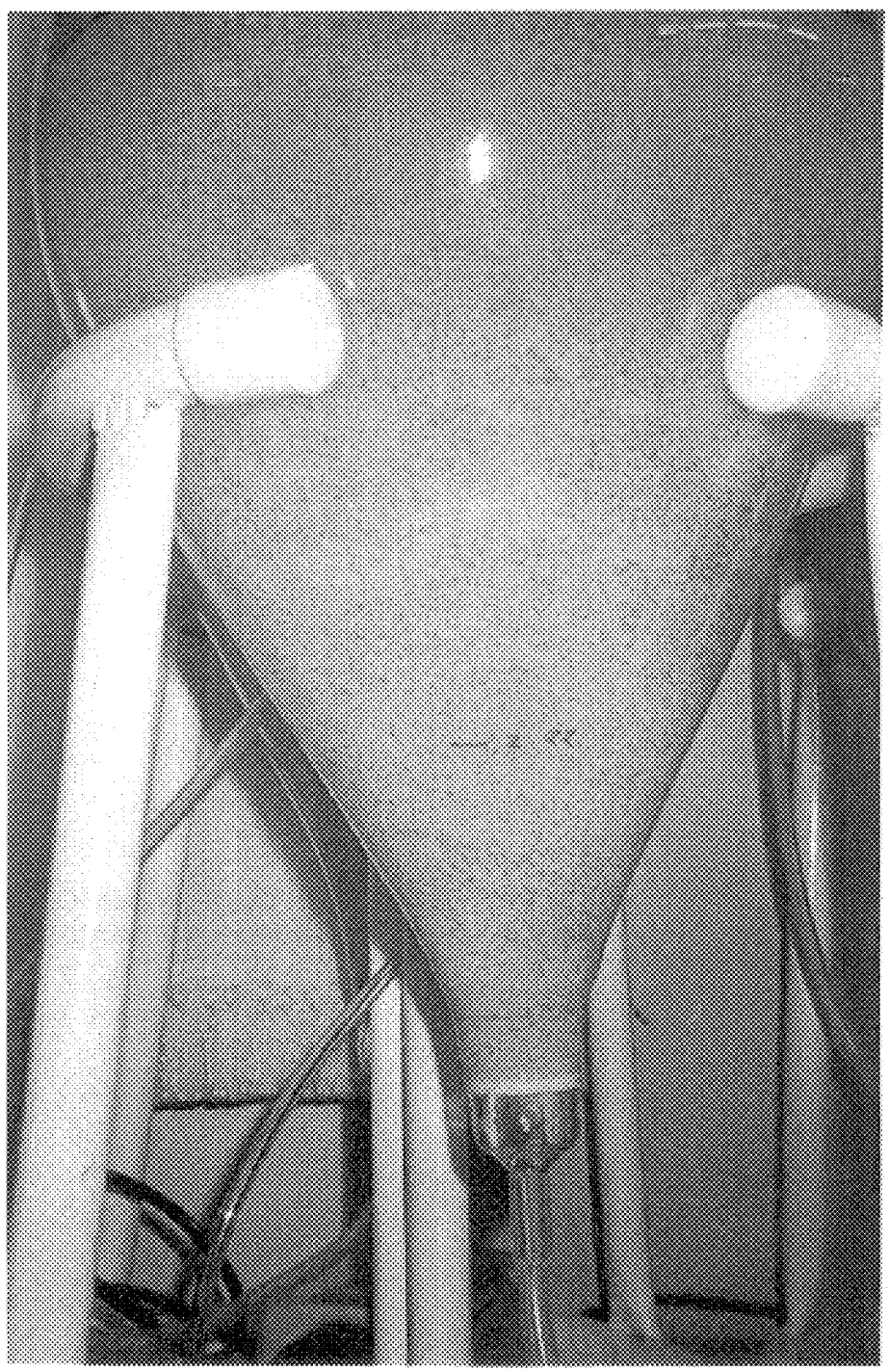
FIG. 3 is a photograph showing homogeneous somatic embryos cultured in a bioreactor during the development of somatic embryos.

It took about 2~3 weeks for most of cell clusters to be developed to globular embryos, which was relatively long compared with a period of the later stage of the somatic embryo development. Thus, there coexisted the cell clusters and the globular embryos in a subculture which was obtained after 2 weeks. In order to classify the mixture into those which were of homogeneous sizes, the subculture was allowed to stand for 1~2 min. for globular embryos to settle down, after which the medium was scanted to another bioreactor. Light cell clusters were transferred to the bioreactor, together with the medium, while most of the remainders were the globular embryos, heavier than the cell clusters. Like this, the synchronous subculture taking advantage of gravity allowed relatively homogeneous sizes of somatic embryos to be collected in a bioreactor during the development of somatic embryos as shown in FIG. 3. The bioreactors used were structured to allow germ-free air to be introduced to their lower parts with the aid of compressors or air pumps for aquaria, as shown in FIG. 1. For the germ-free air, the airlifts employed filters with a pore size of not more than 0.2 µm(Midisart 2000, Sartorius).

The somatic embryos of Eleutherococcus senticosus were developed to somatic embryos of uniform sizes of a torpedo stage or a cotyledonary stage in MS medium without plant growth regulators with subculturing every 2 or 3 weeks. Somatic embryos in a torpedo shape stage or cotyledon shape stage were allowed to grow in MS medium (2% sugar) without plant growth regulators in a 3~10 L bioreactor.

As for the amount of the somatic embryos fed into the bioreactors, it was 20 g for the reactor with a volume of 3 L, 40 g for the reactor with a volume of 5 L, and 80 g for the reactor with a volume of 10 L. The culturing of the somatic embryos was conducted at 25_1° C. in a place which was light, but did not allow direct sunlight to stream thereinto, at daytime and was illuminated by fluorescent light at night. Under these conditions, the culturing for a period of about 10~15 days led the somatic embryos to the development of post-cotyledonary stage.

Figure 4:
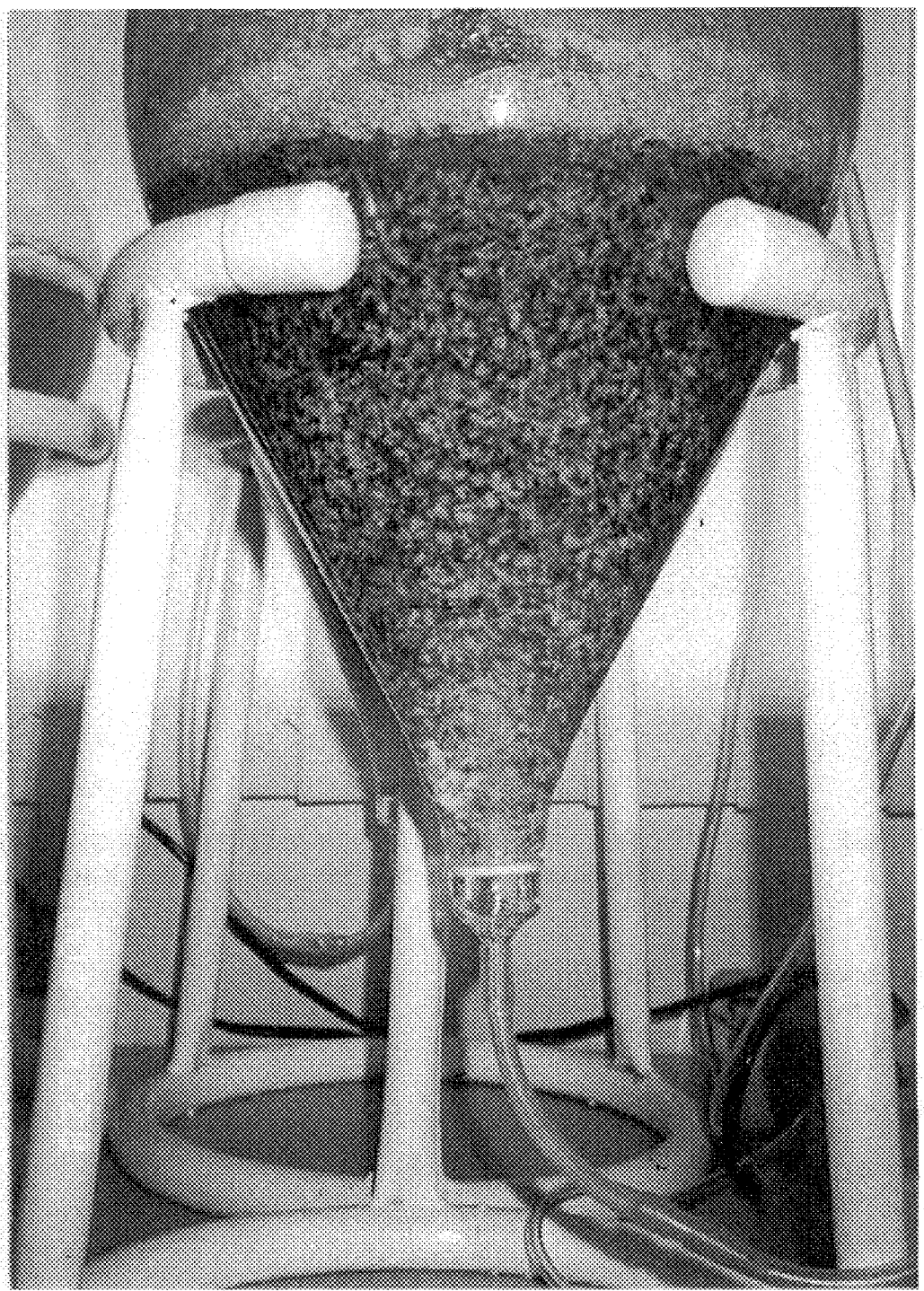
FIG. 4 is a photograph showing the *Eleutherococcus senticosus*/seedlings or plantlets which are cultured in a bioreactor.

As the somatic embryos were further developed to a post-cotyledonary stage, the medium was used at an amount less by one third upon subculturing than that used where young somatic embryos were cultured. Under this condition, the period of the subculturing was reduced from 3 weeks to 2 weeks and a great quantity of seedlings or plantlets, pale green, were obtained as shown in FIG. 4. It took about 25~30 days for the somatic embryos to grow to seedlings or plantlets when being cultured in a bioreactor. In contrast, a period of about 50~60 days was needed for the growth of the cotyledonary embryos to the seedlings or plantlets through suspension culturing. Therefore, the culturing in a bioreactor could reduce the growth period to a half level compared with the suspension culturing.

Figure 5:
FIG. 5 is a photograph showing the seedlings or plantlets grown on an agar plate, which can be commercialized as health foods.

Of the seedlings or plantlets, developed in the liquid medium, those which had healthy cotyledons and roots were aseptically transferred on 1.0% agar medium solidified with deionized water in disposable petridishes at an amount of about 3~4 g per dish, followed by culturing at 25_1° C. for 3~4 days to identify whether the seedlings or plantlets were contaminated or not, as shown in FIG. 5. The seedlings or plantlets, if free of germs, were packaged into goods which were found to be able to be commercialized because they could be stored for one month at 8~12° C.

The *Eleutherococcus senticosus*/seedlings or plantlets cultured in the bioreactors can be immediately used for extracting useful components therefrom or lyophilized in a freeze drier. The lyophilized seedlings or plantlets can be eaten, as they are, or powered for use in health beverages or tea.

As described hereinbefore, the present invention provides a method for mass producing clean, germ-free seedlings or plantlets of *Eleutherococcus senticosus* in an airlift bioreactor.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for culturing *Eleutherococcus senticosus*/seedlings or plantlets, comprising the steps of:

subculturing embryogenic cells KCTC 0504BP to homogeneous sizes of somatic embryos in liquid medium; and culturing the somatic embryos in a bioreactor equipped with an airlift to produce the seedlings or plantlets.

2. A method as set forth in claim 1, wherein said subculturing step is repeatedly carried out every 2~3 weeks.

3. A method as set forth in claim 1, wherein said airlift functions to introduce germ-free air to a lower part of the bioreactor, said germ-free air being produced by passing air through a filter.

4. A method for culturing *Eleutherococcus senticosus*/seedlings or plantlets, comprising the steps of:

suspension or bioreactor culturing of *Eleutherococcus senticosus*/embryogenic cells KCTC 0504BP in liquid medium under a dark condition to allow the mass proliferation of the embryogenic cells;

classifying the proliferated cells according to sizes by passing them through a network;

repeating the above two steps with the embryogenic cells which pass through the network; and bioreactor culturing in liquid medium the embryogenic cell clusters which are entrapped in the network to obtain the *Eleutherococcus senticosus*/seedlings or plantlets.

* * * * *